(12) United States Patent
Hoarau

(10) Patent No.: US 8,971,979 B2
(45) Date of Patent: Mar. 3, 2015

(54) MEDICAL SENSOR FOR REDUCING MOTION ARTIFACTS AND TECHNIQUE FOR USING THE SAME

(75) Inventor: Carine Hoarau, Lafayette, CA (US)

(73) Assignee: Covidien LP, Mansfield, MA (US)

( * ) Notice: Subject to any disclaimer, the term of this patent is extended or adjusted under 35 U.S.C. 154(b) by 302 days.

(21) Appl. No.: 13/544,263

(22) Filed: Jul. 9, 2012

(65) Prior Publication Data

US 2012/0277560 A1 Nov. 1, 2012

Related U.S. Application Data

(63) Continuation of application No. 12/836,306, filed on Jul. 14, 2010, now Pat. No. 8,260,391, which is a continuation of application No. 11/225,295, filed on Sep. 12, 2005, now abandoned.

(51) Int. Cl.
*A61B 5/1455* (2006.01)
*A61B 5/00* (2006.01)

(52) U.S. Cl.
CPC .......... *A61B 5/6826* (2013.01); *A61B 5/14552* (2013.01); *A61B 5/6838* (2013.01); *A61B 5/7207* (2013.01)
USPC ............................ 600/344; 600/323; 600/340

(58) Field of Classification Search
USPC .................................. 600/310, 322, 323, 344
See application file for complete search history.

(56) References Cited

U.S. PATENT DOCUMENTS

| | | |
|---|---|---|
| 4,289,141 A | 9/1981 | Cormier |
| 4,471,538 A | 9/1984 | Pomeranz et al. |
| 4,685,464 A | 8/1987 | Goldberger et al. |
| 5,416,582 A | 5/1995 | Knutson et al. |
| 5,919,133 A | 7/1999 | Taylor et al. |
| 6,075,610 A | 6/2000 | Ueda et al. |
| 6,334,065 B1 | 12/2001 | Al-Ali et al. |
| 6,461,305 B1 | 10/2002 | Schnall |
| 6,707,257 B2 | 3/2004 | Norris |
| 6,714,804 B2 | 3/2004 | Al-Ali et al. |
| 6,898,452 B2 | 5/2005 | Al-Ali et al. |
| 6,939,307 B1 | 9/2005 | Dunlop |
| 7,024,235 B2 | 4/2006 | Melker et al. |
| 7,072,705 B2 | 7/2006 | Miga et al. |
| 7,127,278 B2 | 10/2006 | Melker et al. |
| 7,238,159 B2 | 7/2007 | Banet |
| 2004/0059209 A1 | 3/2004 | Al-Ali et al. |
| 2005/0197551 A1 | 9/2005 | Al-Ali et al. |
| 2006/0009700 A1 | 1/2006 | Brumfield et al. |
| 2006/0025931 A1 | 2/2006 | Rosen et al. |
| 2006/0258923 A1 | 11/2006 | Al-Ali et al. |
| 2006/0258924 A1 | 11/2006 | Al-Ali et al. |
| 2006/0258925 A1 | 11/2006 | Al-Ali et al. |
| 2006/0270920 A1 | 11/2006 | Al-Ali et al. |
| 2006/0272418 A1 | 12/2006 | Maris et al. |
| 2006/0272419 A1 | 12/2006 | Maris et al. |
| 2006/0281983 A1 | 12/2006 | Al-Ali et al. |
| 2007/0027375 A1 | 2/2007 | Melker et al. |

FOREIGN PATENT DOCUMENTS

| | | |
|---|---|---|
| EP | 996358 | 1/2002 |
| WO | 9851212 | 11/1998 |
| WO | 2006132862 | 12/2006 |

*Primary Examiner* — Eric Winakur
(74) *Attorney, Agent, or Firm* — Fletcher Yoder PC

(57) ABSTRACT

A sensor may be adapted to reduce motion artifacts by damping the effects of outside forces and sensor motion. A sensor is provided with a motion damping structure adapted to reduce the effect of motion of a sensor emitter and/or detector. Further, a method of damping outside forces and sensor motion is also provided.

13 Claims, 4 Drawing Sheets

MEDICAL SENSOR FOR REDUCING MOTION ARTIFACTS AND TECHNIQUE FOR USING THE SAME

CROSS-REFERENCES TO THE RELATED APPLICATIONS

This Application is a continuation of U.S. patent application Ser. No. 12/836,306, filed Jul. 14, 2010, which is a continuation of U.S. patent application Ser. No. 11/225,295, filed Sep. 12, 2005, the disclosures of which are hereby incorporated by reference in their entirety for all purposes.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Pulse oximetry readings depend on pulsation of blood through the tissue. Thus, any event that interferes with the ability of the sensor to detect that pulsation can cause variability in these measurements. Motion artifacts occur when a patient's movements cause interference in the signal detected by the sensor. Motion artifacts can also occur in response to outside forces acting on the sensor. For example, a patient may be jostled by healthcare workers in emergency room settings. The type of force acting on a sensor will determine the nature of the motion artifact.

Generally, sensors are vulnerable to motion artifacts when the optical distance, or path length, between a sensor's emitter and detector varies due to an undesired mechanical change in the conformation of the sensor while in use. The mechanical deformation of the sensor may be in the form of a compression of the sensor, causing a decrease in path length. Alternately, a sensor may flex or move in a manner that increases the distance between an emitter and detector, resulting in an increase in path length. In any case, variability in the optical path length due to motion can cause motion artifacts and obscure the desired pulse oximetry signal.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes a sensor body, and an emitter and a detector disposed on the sensor body. The sensor also includes a motion damping structure associated with the sensor body, whereby the motion damping structure is adapted to damp a force experienced by the sensor body.

There is also provided a pulse oximetry system that includes: a pulse oximetry monitor; and a pulse oximetry sensor adapted to be operatively coupled to the monitor. The sensor includes a sensor body, and an emitter and a detector disposed on the sensor body. The sensor also includes a motion damping structure associated with the sensor body, whereby the motion damping structure is adapted to damp a force experienced by the sensor body.

There is also provided a method of operating a sensor that includes damping a mechanical force affecting a sensor such that an effective force experienced by at least one of a emitter or a detector is less than the mechanical force.

There is also provided a method of manufacturing a sensor that includes providing a sensor body on which an emitter and a detector are disposed. The method also includes providing a motion damping structure disposed on the sensor body.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1A:
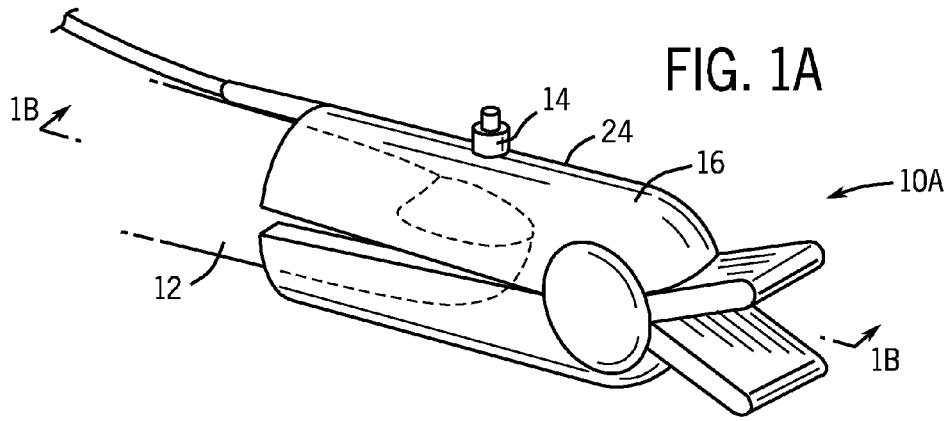
FIG. 1A illustrates a perspective view of an exemplary embodiment of a clip-style pulse oximetry sensor featuring a dashpot.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, sensors for pulse oximetry or other applications utilizing spectrophotometry are provided that reduce motion artifacts by damping the effects of patient movement or outside forces. For example, sensors are provided that have various motion damping mechanisms adapted to reduce the effect of motion or outside forces on a pulse oximetry measurement.

Motion artifacts in pulse oximetry are often generated by the movement of the pulse oximetry sensor relative to the optically probed tissue, which is typically caused by patient movement. Because pulse oximetry is often used in settings where it is difficult to prevent patient motion, it is desirable to provide a mechanism for reducing the effects of motion on the pulse oximetry measurement. For example, a squeezing motion by a patient may mechanically deform a sensor, causing the sensor's emitter and detector to change position relative to one another, resulting in a motion artifact. The squeezing motion may be damped by converting the mechanical energy of patient movement into thermal energy by damping the force with an impact-absorbing fluid or solid, thus dissipating the force and reducing mechanical deformation of the sensor. The force of squeezing may be damped such that the effective force experienced by the sensor's emitter and/or detector is reduced, and the relative change in the position of the emitter relative to the detector is also reduced. Similarly, outsides forces, such as the mechanical force of an object pressing against a sensor, can be damped by absorbing the force such that the effective force experienced by the sensor components is reduced.

Mechanical forces, including those caused by translational and/or kinetic energy of an object, may be impeded by opposing forces. Specifically, as a force acts on a pulse oximetry sensor, it is opposed by the inertia of the sensor as well as the opposing force of a damper. The amplitude of the mechanical energy of movement is attenuated through energy lost to inertia and damping. For example, energy may be lost to viscous damping with a fluid, or by yielding or plastic straining of a damping material. Additionally, some energy will be converted to thermal energy through frictional forces.

Figure 1B:
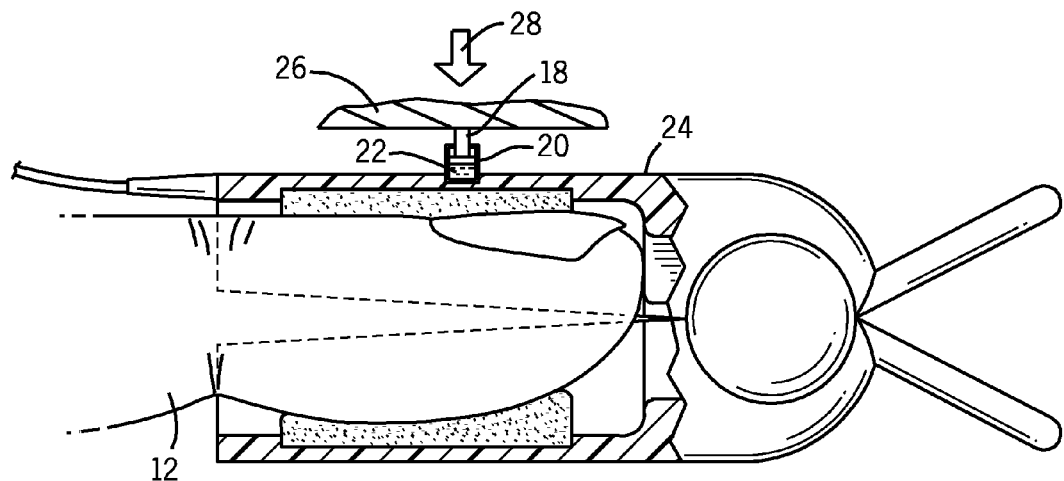
FIG. 1B illustrates a cross-sectional view of the pulse oximetry sensor of FIG. 1A applied to a patient digit that is pressing against an object.

Sensors are disclosed herein having a motion damping mechanism to reduce the effect of motion or outside forces on the measurements of physiological parameters, such as pulse oximetry measurements. FIG. 1A illustrates an exemplary clip-type sensor 10A appropriate for use on a patient's digit 12. The sensor 10A has a dashpot 14 disposed on the sensor body 16, a cross-sectional view of which is illustrated in FIG. 1B. A dashpot 14 is a mechanical device used to damp motion that includes a piston 18 that moves through a cylinder 20 containing a fluid 22. The dashpot 14 is partially embedded in the sensor body 16 such that the piston 18 protrudes from the sensor body 16 on a surface 24 that does not contact the sensor site of the patient's tissue during normal use. A force applied to the piston 18, such as tapping against an object 26, causes the piston 18 to move through the fluid 22 in the direction shown by arrow 28. As the piston 18 pushes through the fluid 22, the mechanical energy of the force acting on the piston 18 is converted into thermal energy. The damping force is proportional to the velocity of the piston 18 and the viscosity of the fluid 22 through which the piston moves. Thus, the dashpot 14 damps motion caused by tapping or pressing the sensor 10A against an object 26.

In other embodiments (not shown), the sensor 10A may have multiple dashpots 14 disposed on the sensor body 16 on the surface 24 that does not contact the sensor site of the patient's tissue during normal use. It may be advantageous to provide motion damping mechanisms on multiple sides of the sensor 10A, as it is difficult to predict the types of motion that the sensor 10A may experience. For example, dashpots 14 may be distributed on the sensor body 16 in locations directly opposing each other across the digit 12. Further, it should be understood that a dashpot 14 according to the present technique may be adapted to damp forces applied at various angles. The piston 18 may be adapted move through the fluid 22 at an angle that corresponds to the angle with which the force was applied.

Figure 2:
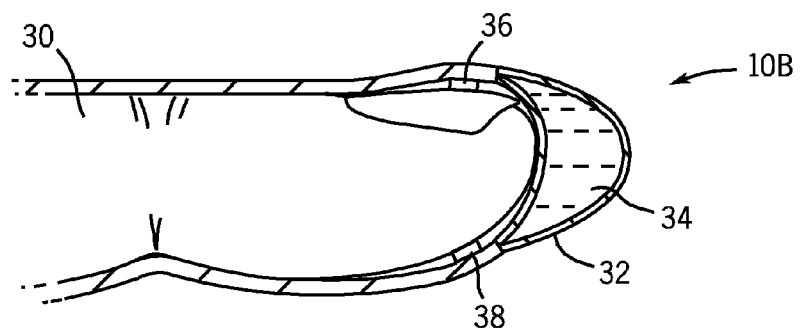
FIG. 2 illustrates a cross-sectional view of an exemplary embodiment of a bandage-style pulse oximetry sensor applied to a patient's digit, whereby the sensor includes an impact-absorbing chamber at one end of the sensor.

In certain embodiments, a fluid may used to damp mechanical energy by other techniques. For reasons related to total sensor weight, it may be desirable to employ a lightweight motion damping device in conjunction with disposable sensors. For example, FIG. 2 illustrates a bandage-type sensor 10B applied to a patient digit 30. The sensor 10B has an impact-absorbing chamber 32 that contains a fluid 34. As depicted, the impact-absorbing chamber 32 is disposed on the sensor 10B such that it correlates with the fingertip region of the digit 30. The fluid 34 in the impact-absorbing chamber 32 damps energy caused by pressing or tapping a fingertip against an object. The impact-absorbing chamber 32 is flexible and not completely filled with fluid, and is thus compressible in response to an applied force. The mechanical energy of the pressing or tapping is damped through conversion to thermal energy and/or absorbed by the physical deformation of the fluid in an amount proportional to the force applied. Thus, the motion is damped and the effective force experienced by the emitter 36 and the detector 38 is reduced as a consequence.

Figure 3:
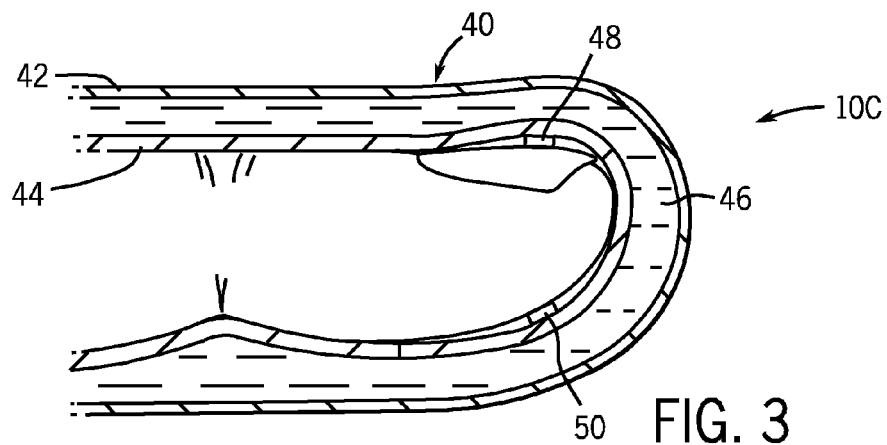
FIG. 3 illustrates a perspective view of an alternate exemplary embodiment of a bandage-style pulse oximetry sensor with a fluid-filled impact-absorbing chamber disposed along the body of the sensor.

In another embodiment, as shown in FIG. 3, an impact-absorbing chamber 42 may be disposed on a sensor 10C such that the impact-absorbing chamber 42 covers the surface 40 of the sensor body 44 that does not contact the tissue during normal use. The fluid 46 in the impact-absorbing chamber 42 will physically impede a finger squeezing motion as well as damp the mechanical energy associated with the motion. As the energy of squeezing is absorbed by the fluid 46, the sensor 10C remains substantially stable. As a consequence, the emitter 48 and the detector 50 also remain substantially unaffected by the motion.

Figure 4:
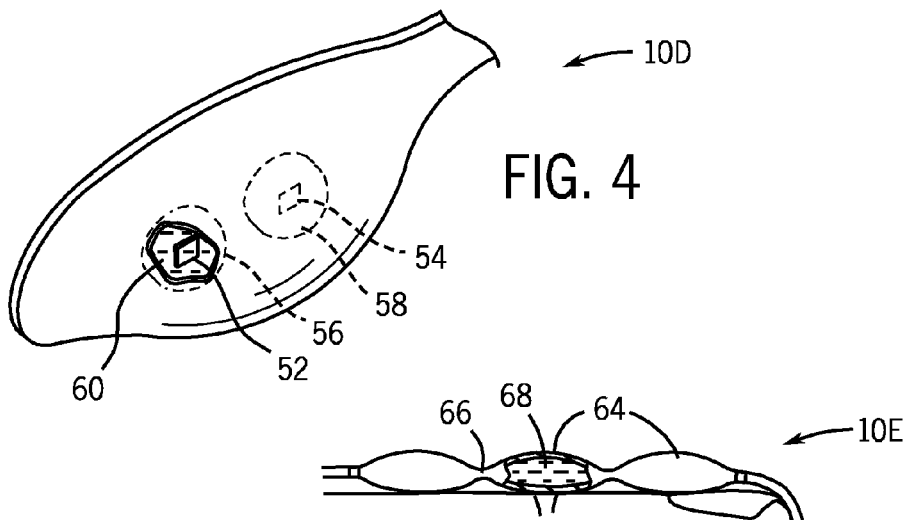
FIG. 4 illustrates a perspective view of an exemplary embodiment of a forehead pulse oximetry sensor whereby the emitter and detector are disposed within impact-absorbing chambers.

It is also contemplated that a fluid may damp mechanical energy to reduce its direct action on an emitter 52 or a detector 54. FIG. 4 illustrates a reflectance-type sensor 10D adapted for use on a patient's forehead. The sensor 10D has impact-absorbing chambers 56 and 58 containing a fluid 60. The impact-absorbing chambers 56 and 58 enclose an emitter 52 and a detector 54, respectively. The emitter 52 and the detector 54 are surrounded by the fluid 60, which absorbs outside forces, thereby reducing the transmission of outside forces to the emitter 52 and the detector 54. The impact-absorbing chambers 56 and 58 also protect the emitter 52 and the detector 54 from damage during the period of use of the sensor 10D. Such an arrangement may be advantageous in outpatient situations in which it is contemplated that a patient may be ambulatory, and the sensor 10C may be subject to higher-than-normal outside forces.

Figure 5A:
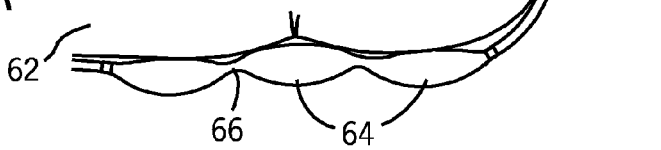
FIG. 5A illustrates a cross-sectional view of an exemplary embodiment of a bandage-style pulse oximetry sensor having a series of interconnected impact-absorbing chambers.
Figure 5B:
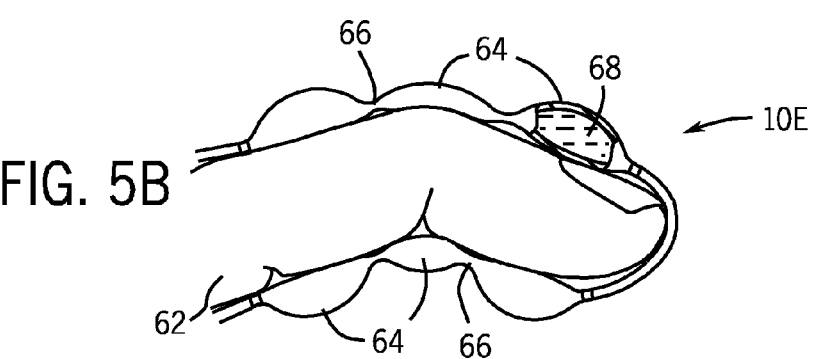
FIG. 5B illustrates a cross-sectional view of the pulse oximetry sensor of FIG. 5A applied to a patient digit that is flexed at the first finger joint.

In another embodiment, FIG. 5A illustrates an exemplary bandage-style sensor 10E adapted for use on a digit 62. The sensor 10E has a plurality of impact-absorbing chambers 64 connected by respective orifices 66, wherein the orifices 66 are sized so as to restrict the flow rate of a fluid 68 between the impact-absorbing chambers 64. As shown in FIG. 5B, as the digit 62 moves in a squeezing motion, the fluid 68 passes through the orifices 66 and is redistributed through the impact-absorbing chambers 64 in response to the movement. The impact-absorbing chambers 64 are partially full of the fluid 68. The redistribution of the fluid 68 serves to damp the energy generated by the digit 62 moving in space. Specifically, the force of the digit 62 movement is opposed by the force required to push the fluid 68 through the orifices 66. The damped force experienced by the sensor 10E is thus reduced by roughly the amount of the opposing force provided by the damping mechanism.

The fluid (e.g. fluid 22, fluid 34, fluid 46, fluid 60, or fluid 68) described in the above embodiments may be any suitable fluid with the appropriate rheological properties for damping mechanical energy, such as a viscoelastic fluid or gel. In certain embodiments, the fluid may be air or other gases and gas mixtures. In other embodiments, the fluid may be an oil or liquid, such as mineral oil. Other examples of suitable fluids include, but are not limited to, polyethylene glycol, liquid silicone, magnetorheological fluids, and polyurethane polymer gels. It is contemplated that the fluid may be a mixture of liquid and gas. In certain embodiments, it may be desirable employ a gas or gas mixture for reasons related to cost, manufacturing convenience, and total sensor weight. In situations where a sensor may be exposed to more extreme outside forces, it may be desirable to employ a viscoelastic oil, as oils generally provide more efficient damping than gases.

Figure 6A:
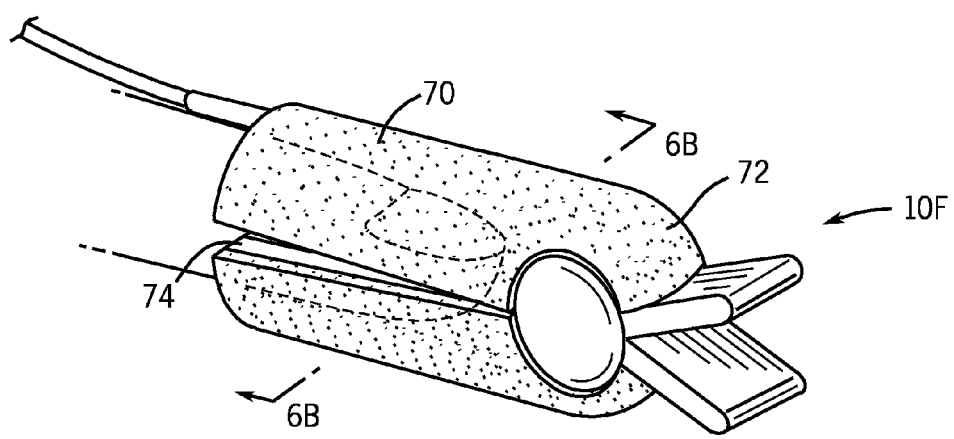
FIG. 6A illustrates a perspective view of an embodiment of an exemplary clip-style pulse oximetry sensor with an impact-absorbing foam disposed on the surface that does not contact a patient's tissue during normal use according to the present invention.
Figure 6B:
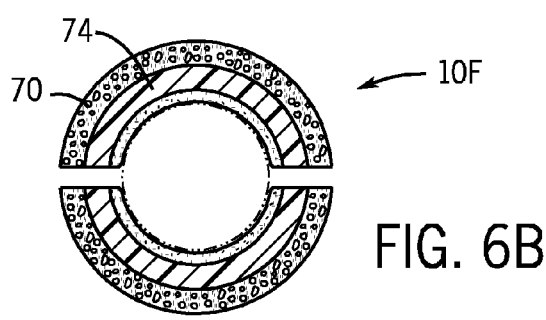
FIG. 6B illustrates a cross-sectional view of the pulse oximetry sensor of FIG. 6A.

In certain embodiments, impact-absorbing solids and/or foams with viscoelastic properties may be appropriate for mechanical damping of motion to reduce motion artifacts in a pulse oximetry sensor. For example, a clip-style sensor 10F is illustrated in FIG. 6A that has an impact-absorbing foam 70 disposed over a non-tissue-contacting surface 72 of the sensor body 74. FIG. 6B is a cross-sectional view of the sensor 10F. The impact-absorbing foam 70 dissipates the effect of an outside force on the sensor 10F. In another embodiment (not shown), the impact absorbing foam 70 is disposed on the tissue-contacting surface of the sensor 10F. Impact-absorbing solids and foams according to the present invention include, but are not limited to, neoprene, silicone, rubber, Sorbothane® (available from Sorbothane, Incorporated), and ISODAMP® SD or CONFOR® foams (available from E-A-R Specialty Composites).

Figure 7:
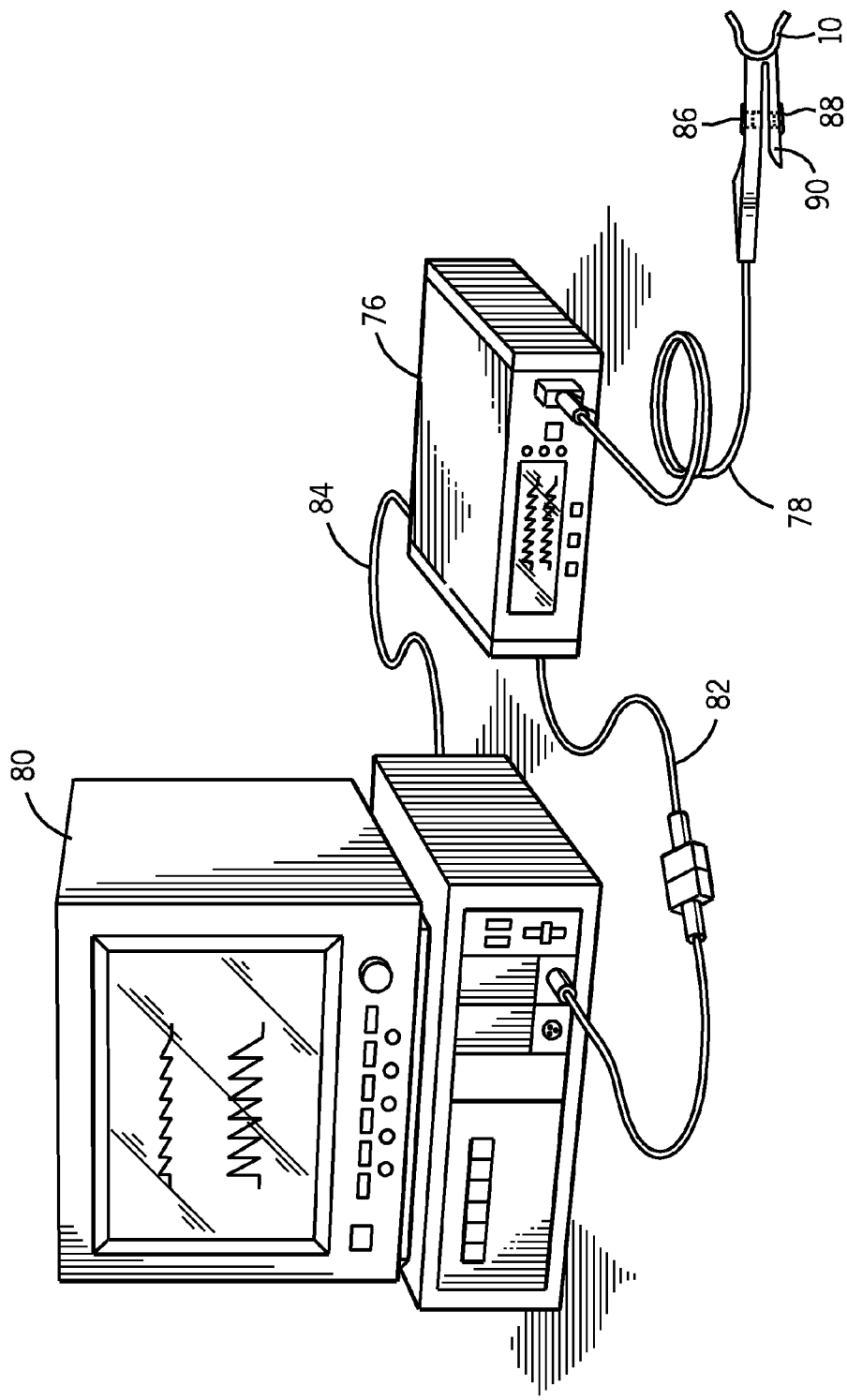
FIG. 7 illustrates a pulse oximetry system coupled to a multi-parameter patient monitor and a sensor according to embodiments of the present invention.

A sensor, illustrated generically as a sensor 10, may be used in conjunction with a pulse oximetry monitor 76, as illustrated in FIG. 7. It should be appreciated that the cable 78 of the sensor 10 may be coupled to the monitor 76 or it may be coupled to a transmission device (not shown) to facilitate wireless transmission between the sensor 10 and the monitor 76. The monitor 76 may be any suitable pulse oximeter, such as those available from Nellcor Puritan Bennett Inc. Furthermore, to upgrade conventional pulse oximetry provided by the monitor 76 to provide additional functions, the monitor 76 may be coupled to a multi-parameter patient monitor 80 via a cable 82 connected to a sensor input port or via a cable 84 connected to a digital communication port.

The sensor 10 includes an emitter 86 and a detector 88 that may be of any suitable type. For example, the emitter 86 may be one or more light emitting diodes adapted to transmit one or more wavelengths of light in the red to infrared range, and the detector 88 may be a photodetector selected to receive light in the range or ranges emitted from the emitter 86. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

The emitter 86 and the detector 88 may be disposed on a sensor body 90, which may be made of any suitable material, such as plastic, foam, woven material, or paper. Alternatively, the emitter 86 and the detector 88 may be remotely located and optically coupled to the sensor 10 using optical fibers. In the depicted embodiments, the sensor 10 is coupled to a cable 78 that is responsible for transmitting electrical and/or optical signals to and from the emitter 86 and detector 88 of the sensor 10. The cable 78 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 86 and detector 88 that are typically placed on opposing sides of the sensor site. If the sensor site is a fingertip, for example, the sensor 10 is positioned over the patient's fingertip such that the emitter 86 and detector 88 lie on either side of the patient's nail bed. In other words, the sensor 10 is positioned so that the emitter 86 is located on the patient's fingernail and the detector 88 is located 180° opposite the emitter 86 on the patient's finger pad. During operation, the emitter 86 shines one or more wavelengths of light through the patient's fingertip and the light received by the detector 88 is processed to determine various physiological characteristics of the patient. In each of the embodiments discussed herein, it should be understood that the locations of the emitter 86 and the detector 88 may be exchanged. For example, the detector 88 may be located at the top of the finger and the emitter 86 may be located underneath the finger. In either arrangement, the sensor 10 will perform in substantially the same manner.

Reflectance type sensors generally operate under the same general principles as transmittance type sensors. However, reflectance type sensors include an emitter 86 and detector 88 that are typically placed on the same side of the sensor site. For example, a reflectance type sensor may be placed on a patient's fingertip or forehead such that the emitter 86 and detector 88 lie side-by-side. Reflectance type sensors detect light photons that are scattered back to the detector 88.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, intravascular dyes, and/or water content. Rather, the invention is to cover all modifications, equivalents, and alternatives falling within the spirit and scope of the invention as defined by the following appended claims.

What is claimed is:

1. A sensor comprising:
   a sensor body;
   an impact-absorbing chamber associated with the sensor body, wherein the impact-absorbing chamber is configured to damp a force experienced by the sensor body, wherein the impact-absorbing chamber comprises a fluid, and wherein the fluid comprises a viscoelastic fluid or a gel; and
   an emitter and a detector disposed on the sensor body, wherein at least one of the emitter or the detector is disposed within the impact-absorbing chamber.

2. The sensor, as set forth in claim 1, wherein the sensor comprises a pulse oximetry sensor.

3. The sensor, as set forth in claim 1, wherein the emitter comprises at least one light emitting diode, and wherein the detector comprises at least one photodetector.

4. The sensor, as set forth in claim 1, wherein the sensor is configured to be applied to a forehead of a patient.

5. The sensor, as set forth in claim 1, wherein the sensor body comprises a plastic.

6. A patient monitoring system comprising:
   a patient monitor; and
   a sensor configured to be operatively coupled to the patient monitor, wherein the sensor comprises:
      a sensor body;
      an impact-absorbing chamber associated with the sensor body, wherein the impact-absorbing chamber is configured to damp a force experienced by the sensor body, wherein the impact-absorbing chamber comprises a fluid, and wherein the fluid comprises a viscoelastic fluid or a gel; and
      an emitter and a detector disposed on the sensor body, wherein at least one of the emitter or the detector is disposed within the impact-absorbing chamber.

7. The patient monitoring system, as set forth in claim 6, wherein the sensor comprises at least one of a pulse oximetry sensor or a sensor for measuring a water fraction.

8. The patient monitoring system, as set forth in claim 6, wherein the emitter comprises at least one light emitting diode, and wherein the detector comprises at least one photodetector.

9. The patient monitoring system, as set forth in claim 6, wherein the sensor is configured to be applied to a forehead of a patient.

10. The patient monitoring system, as set forth in claim 6, comprising a cable configured to couple the sensor to the patient monitor.

11. A method of manufacturing a sensor, comprising:
    providing a sensor body; and
    providing an impact-absorbing chamber disposed on the sensor body, wherein the impact-absorbing chamber surrounds at least one of an emitter or a detector associated with the sensor, wherein providing the impact-absorbing chamber comprises providing a chamber comprises a fluid, and wherein the fluid comprises a viscoelastic fluid.

12. The method, as set forth in claim 11, wherein providing the sensor body comprises providing a sensor body configured to be applied to a forehead of a patient.

13. The method, as set forth in claim 11, wherein the sensor comprises at least one of a pulse oximetry sensor or a sensor for measuring a water fraction.

* * * * *